United States Patent [19]

Villa-Real

[11] 4,397,317
[45] Aug. 9, 1983

[54] ELECTRONIC BLOOD PRESSURE AND PULSE RATE CALCULATOR WITH OPTIONAL TEMPERATURE INDICATOR, TIMER AND MEMORY

[76] Inventor: Antony-Euclid C. Villa-Real, 2512 Capistrano Ave., Las Vegas, Nev. 89121

[21] Appl. No.: 141,101

[22] Filed: Apr. 17, 1980

[51] Int. Cl.³ .............................................. A61B 5/02
[52] U.S. Cl. ................................................. 128/680
[58] Field of Search .............................. 128/670–671, 128/680–686, 687–690, 713, 736

[56] References Cited

U.S. PATENT DOCUMENTS

| | | | |
|---|---|---|---|
| 2,603,210 | 7/1952 | Puig | 128/684 |
| 3,480,005 | 11/1969 | Edwards | 128/680 |
| 3,654,915 | 4/1972 | Sanctuary | 128/682 |
| 3,996,928 | 12/1976 | Marx | 128/671 |
| 4,033,336 | 7/1977 | Murawski et al. | 128/682 |
| 4,053,951 | 10/1977 | Hudspeth et al. | 128/670 |
| 4,109,643 | 8/1978 | Bond et al. | 128/666 |
| 4,121,574 | 10/1978 | Lester | 128/736 |
| 4,167,181 | 9/1979 | Lee | 128/682 |
| 4,252,127 | 2/1981 | Gemelke | 128/683 X |
| 4,313,445 | 2/1982 | Georgi | 128/682 |
| 4,320,767 | 3/1982 | Villa-Real | 128/680 |

OTHER PUBLICATIONS

"London Pressurometer Automatic Indirect BP Monitor", Avionics Research Products, 6901 W. Imp. Hgwy., Los Ang., Cal. 90045.
"Sphygmostat Electronic BP Monitor", Tech. Resources Inc., 14 Green St., Waltham, Massachusetts 02154.
Sheppard, L. C. et al., "Surgical ICU Automation", JAAMI, vol. 6, No. 1, Jan.–Feb. 1972.
Kalinsky, D. et al., "The Solo Monitor Microcomputer Bedside Monitor", Computers in Cardiology, Sep. 1979, pp. 461–464.
"PARA Digital Blood Pressure Unit", Palo Alto Rsrch. Assoc., 499 Hamilton Ave., Palo Alto, Cal. 94301.
"MEDTEK 410 BP Monitor", MEDTEK Corp., 6800 Jericho Turnpike, Syosset, N.Y. 11791.

Primary Examiner—Kyle L. Howell
Assistant Examiner—Francis J. Jaworski

[57] ABSTRACT

A portable blood pressure and pulse rate device utilizing coordinated systems of pressure and sound transducers and calibration gauge using LED or LCD readout having an electronically operable pressure threshold setter that can be set about 30 millimeters mercury equivalence or more above the anticipated highest systolic blood pressure of the subject; the pressure threshold is entered into the RAM memory to automatically trigger the electronic sensing and latching of the blood pressure and pulse rate values only after the set pressure threshold has been reached; the degree of physical activity can be independently programmed from the degree of emotional stress through two sets of electronic function levers for storage and future recall of these data respective to the date, time, identification, and other relevant data per patient; right or left arm where blood pressure is taken is programmable. All data can be recalled by synthesized speech and/or visually.

3 Claims, 2 Drawing Figures

ELECTRONIC BLOOD PRESSURE AND PULSE RATE CALCULATOR WITH OPTIONAL TEMPERATURE INDICATOR, TIMER AND MEMORY

BACKGROUND OF THE INVENTION

The instant invention relates to an electronic apparatus for the measurement of systolic and diastolic blood pressures, including temperature indicator, timer, pulse rate calculator and memory.

There are two methods of blood pressure measurements of the human or animal subject; (1) the direct method which employs the insertion of a cannular probe into the blood vessel, while said probe is connected to a blood pressure measuring apparatus, and; (2) the indirect procedure, which is the most widely accepted method in clinical practice that utilizes the compression arm-cuff with the associated components. The latter senses for the "Korotkoff sounds" created by the acoustical turbulence of blood flow through the compressed semi-opened artery such as the brachial artery. When the brachial artery is fully compressed by the arm-cuff, there is no sound detected because of the absence of arterial blood flow below the fully occluded portion of the said compressed artery. As the arm-cuff pressure is gradually released from that state of compression and total arterial occlusion, each cardiac systole delivers an arterial pressure head force that becomes propagated through the semi-opened artery until the critical resistance exerted by the intravascular wall is exceeded by the said arterial pressure head force, at which instant, the first sharp "thud" sound of "Korotkoff" is detected, thereby determining the systolic reading in relation to the millimeters of Hg. of applied cuff pressure registered in the pressure gauge. As the compressed artery undergoes continuous gradual decompression, the "Korotkoff" sounds follow five phases of characteristically differential sounds; (1) first phase characterized by the aforementioned sharp "thud" sound; (2) a second phase characterized by blowing or swishing sounds; (3) a third phase characterized by a softer thud sound than phase 1; (4) a fourth phase with a soft and blowing sound that disappears and; (5) a fifth phase when the sounds completely disappear. The occurrence of the fifth phase is the commonly acceptable diastolic blood pressure reading in the cases wherein only one diastolic measurement is taken. The fourth phase is considered to have certain disadvantages when used to indicate the diastolic level.

The instant invention provides apparatus which permits much more rapid measurement of blood pressures and in which the subjective determinations of the auscultatory technique together with variations which may be due to the different hearing characteristics of administering personnel are entirely eliminated. The measurements with the apparatus of the instant invention are thus less subject to variations and may be made by persons without skill or training. The apparatus, however, is not unduly complicated, bulky, or expensive; and to the extent that it is somewhat more expensive than presently used blood pressure measurement apparatus, the expense is far more than justified by the saving in time of highly trained physicians and nurses.

The apparatus is contemplated primarily for use in the clinical measurement of blood pressure in connection with physical examinations or the like, but it may also be adapted to automatic measurement of blood pressure for purposes of research, automatic monitoring of hospital patients, or for use by athletes in stressed or unstressed condition.

SUMMARY OF THE INVENTION

One object of the instant invention is to provide a small portable electronic blood pressure and pulse rate calculator utilizing an inflatable-deflatable pressure cuff including a detachable acoustical transducer situated inside the said cuff plus a pressure transducer situated inside the main body of the device, wherein the interconnections for both the electrical and pneumatic systems are carried through a common tubing.

Another object is to provide a faster, reliable and accurate blood pressure and pulse rate device that uses an LED or LCD pressure display gauge capable of eliminating the presently used aneroid pressure gauge that has many mechanical parts needing frequent calibrations, as well as having the capability of replacing the fragile mercury manometers used in most doctor's offices, clinics, laboratories and hospitals.

Another object of the present invention is to provide an advanced system having pressure threshold setting means to effect conservation of electrical energy by triggering the activity of the micro-electronic circuitry for the measurement of the systolic and diastolic blood pressures as well as the pulse rate when in the pressure measuring mode, only after the pressure exerted by the optimally placed pressure compression cuff upon the subject's arm has exceeded the manually or electronically set pressure threshold setting.

And yet another object of the invention is to provide an advanced system using micro-electronic circuitry, having analog and digital display means for use in both individual and multi-individual blood pressure and pulse rate calculations, and, equipped with coding means to effect proper entry of date-time-data respective to each individual being tested, and capable of retrieval of the corresponding information from the micro-computer's memory bank; the respective information retrieved, being systematically recalled in either forward or backward sequential order by the use of special function keys.

And yet a further object of the invention is to provide an advanced system using micro-electronic integrated circuitry and having analog and digital visual display means coordinated with audio amplification capabilities for easy triple verification of relevant data.

Yet another object of the present invention is to provide a fast, accurate and reliable data measurement of both blood pressure and pulse rate for easy self-application in the home, office and during travel, as well as for the easy and effective instant measurement of the same by medical personnel.

Moreover, a still further object is to provide a modern blood pressure and pulse rate calculator for use by athletes in the determination of their cardiovascular responses to various degrees of exercise compared to the readings during their relaxed conditions.

Another object is to provide an approximate visual range locator in the analog pressure display gauge, wherein the range between the subject's systolic and diastolic blood pressure, can be seen as a series or continuously latched strand of lighted LED or LCD display as an additional feature of the device for the convenience of the user.

A further object is to provide a device that is capable of logging into the microcomputer's memory, the correct limb location where the blood pressure has been taken, at a specific time and date, and capable of retrieving said data from the memory to the display register.

Another further object is to provide a small-size portable blood pressure and pulse rate calculator, having a coordinated function for synthesized speech as well as magnetic card entry and retrieval system.

Yet another object of the instant invention is to provide means for logging into the device, the levels of both the physical activity and the emotional stress of the tested individual, as well as the retrieval of these data at some future time, in conjunction with other entered data, respective to the I.D. number, date, and time which the user desires to retrieve.

An additional object of the same invention is to provide a device that can be interconnected to a temperature measuring probe and capable of displaying said temperature data of an individual or multiplicity of patients according to the I.D. number, said data capable of being stored and retrieved to and from the microcomputer's memory in accordance with the date and time of said data measurement.

And yet another object of the present invention is to provide a device that can be used as an electronic stethoscope for diagnosing the respiratory conditions of patients and to diagnose the heart murmurs and cardiac irregularity of heart patients, and also to determine the normality of the respiratory and heart conditions of healthy individuals.

DETAILED DESCRIPTION OF THE DRAWINGS

Figure 1:
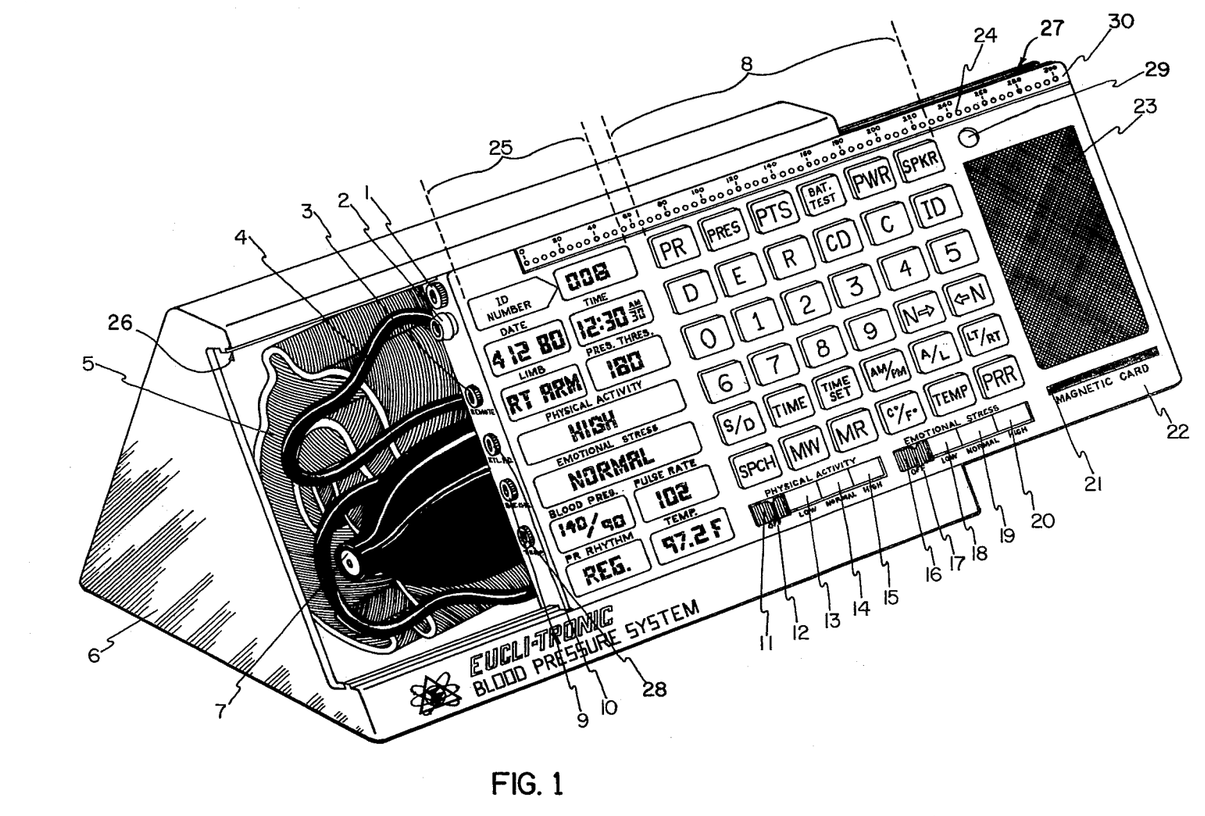
FIG. 1 is a perspective view of the electronic blood pressure device of the instant invention with the storage compartment in a partly open position showing a pressure cuff and pump bulb therein.

FIG. 1 shows a perspective view of the instant invention especially for use in doctors' offices, clinics, laboratories, and hospitals, or for home or office use by one or more individuals. A housing 6 is provided which forms a storage compartment for a pneumatic inflatable pressure cuff 5 which is adapted to be connected to the pump bulb 7, having a one-way inlet valve, through flexible tube 4, said pump bulb is also equipped with a regulatory air-valve for inflating and deflating the air bladder situated inside the non-elastic compression cuff 5. The acoustical transducer, normally placed at an optimal location at the said compression cuff is electrically linked through electrical wiring enclosed in a tubing to electrical socket 1, in order to electrically activate the systolic and diastolic latching at the LED pressure gauge as well as at the relevant systolic and diastolic and pulse rate and/or pulse rate rhythm displays at 25 during the blood pressure plus pulse rate and pulse rate rhythm measuring mode of the device. The actual compression pressure exerted by the said cuff is directly relayed through the rubber tubing which is coupled to 2 which receives the pneumatic triggering of the pressure load from the compression cuff depending upon its compression degree upon the tissues surrounding the subjected pressurized artery; said pressure load is exerted upon a factory calibrated spring having the same pressure equivalence expressed in millimeters of mercury compared to the regular blood pressure apparatuses in existence, and that depending upon the degree of pressure exerted upon the said factory calibrated spring having a zero point of non-displacement starting from the beginning prior to the activation of the compression cuff, there is a corresponding directly proportional voltage generated depending upon the preset coacting pressure transducer such as a Hall-effect transducer which via the system electronics triggers the electrical activation of the LED pressure gauge either in an upward or downward manner across the pressure calibration face 24.

The rubber tubing 4 carries both the electrical wiring from the acoustical transducer to be coupled with the electrical socket 1 and also the pneumatic channel from the internal air bladder situated inside the non-elastic compression cuff to be coupled to pneumatic pressure receptor 2 which will activate the linear displacement of the Hall-effect transducer to effect the proper measurement of the compression pressure exerted by the compression cuff and registered at the LED pressure gauge 24.

The housing compartment 6 is closed and opened by sliding the panel which contains the main display 25 and the function keys 8 along the complimentary rail 26 and channel 27.

At 25 are shown all the various independent digital displays for "I.D. NUMBER", "DATE", "TIME", "LIMB", "PRESSURE THRESHOLD", "PHYSICAL ACTIVITY", "EMOTIONAL STRESS", "BLOOD PRESSURE", "PULSE RATE", "PULSE RATE RHYTHM", and "TEMPERATURE". The function keys are generally indicated at 8 and will be hereinafter further described.

The function key which is labeled PR is for pulse rate, PWR for power, CLR for clear, BAT TEST for battery test, S/D for systolic and diastolic, PRES for pressure of the compression cuff and SPKR for speaker. The system is activated by pushing or depressing the PWR function key. When the device is connected through the home electrical outlet, the device gets its power from the available AC current. However, if the device is disconnected from the home electrical power, it operates on the battery supply internally located in the device. In order to check for the optimal level of energy from the battery pack, the function key BAT TEST which is a momentary off/on function key is depressed. After depressing the said function key an adequate load is drawn from the battery pack while measuring the voltage and the current rate of change of the battery energy supply, during which time a continuous sound from 23 which is the speaker, is heard, and at the same time a continuous light appears at LED 29, which means that there is an adequate supply of energy coming from the batteries to operate the device in an optimal manner. However, if a beeping sound is heard through the speaker 23 and an intermittent light is generated or seen at 29, this warning indicates that the battery power is getting low and a replacement or recharging of the battery pack is essential in order to maintain optimal functional capabilities of the device. When the system is used primarily for determining only the pulse rate or the heart rate of the subjected individual, the PR function key must be depressed in the "ON" position so that the system, especially the removable acoustical transducer can be detached from the normal placement at the compression cuff 5 and then the said acoustical transducer can be placed in direct contact with the radial artery or may be placed therearound the left portion of the chest where the heart sounds are dominant so that the acoustical transducer detects the pulse rate from the radial artery or the heart beats from the chest in a manner as that of a high powered electronic stethescope. In this stethoscopic mode of the operation of the device, the respiratory sounds including the respiratory rales in cases of respiratory inflammatory conditions can also be detected through the speaker in an adequately amplified manner.

The compression arm cuff can be specially designed so that the nonelastic portion can have a zipper type opening and closing means so as to be able to properly engage or disengage the acoustical transducer to and from the said proper location at the compression arm cuff.

The pulse rate reading is an electronic calculation of the number of pulse beats per minute during a certain short time frame even though the actual period of time measurement is not exactly one minute. When measuring the systolic and diastolic blood pressure readings, the function key S/D which is a permanent off/on button, must be depressed in the "ON" position in order to activate the system so as to properly latch the corresponding systolic and diastolic digital readings at the systolic and diastolic register window. The function key "PRES" which is a permanent off/on button for pressure, must be depressed in order that the LED pressure display gauge will be activated. When the cuff means is inflated against the upper arm at the bicep area where the brachial artery is located, the Hall-effect transducer generates a proportional voltage depending upon the compression degree exerted by the pressure cuff means 5 against the tissues over the brachial artery. The degree of pressure exerted against the tissues by the pressure cuff means 5 becomes translated to corresponding voltage levels which activates the microcomputer to demonstrate an analog representation of the pressure exerted at the LED pressure gauge 24. This analog representation is seen by the user as a traveling LED activation, either in an increasing or decreasing fashion, at the calibrated gauge. When the user of the device has familiarized himself or herself in the proper use of the pressure cuff means, by way of attaining an optimal degree of confidence in exerting the proper rate of compression during blood pressure and pulse rate testing by watching the emitted light signals generated at pressure gauge 24, he or she may decide to turn off the function key PRES for pressure, by quickly depressing function button PRES to return to its original undepressed "OFF" position, and then entirely rely upon the registration of the corresponding systolic and diastolic digital readouts. The tester is covered by a transparent cover 30 having optical magnifying properties in order that the numerals 0 to 300 including the equidistantly positioned LEDs can easily be seen as larger images, thus achieving better visual aid for elderly individuals. When function keys PR and SPKR are depressed in the "ON" position, the system can be utilized for the audio-visual detection of both the heart and the pulse beats, thereby effecting an additional audible determination of whether or not the heart beats or the pulse beats are irregular or regular in occurrence, aside from achieving the dynamic digital readings of the heart rate or pulse rate per minute. The PRR function key must also be depressed in the "ON" position to be able to determine and display the regularity or irregularity of the pulse rate or heart rate. The system can also be used in conjunction with the detection of the occurrence of the Korotkoff sounds, from the first phase of sound appearance to the fifth phase when the said Korotkoff sounds disappear during the concurrent determination of the systolic, diastolic, and pulse rate readings when operating the device under the pressure measuring mode. Another use of activating the speaker function key SPKR, is to be able to audibly hear the amplified unfiltered sounds of respiratory rales or other sounds of congestive nature that are evident in certain cases of respiratory infections or allergic reactions, when the device is not in the pressure measuring mode. Therefore, the use of speaker 23 from where the amplified sounds emanate as activated by speaker function key can be likened to a high powered stethoscope as mentioned before, but without connecting an ear piece to the listener's ear while attaining greater audio amplification.

During the blood pressure and pulse rate detection mode effected by the activation of the S/D function key, the microcomputer detects and enables the first Korotkoff sound only after the pressure threshold setting which was previously adjusted has been exceeded by the compression pressure exerted by the compression cuff. This procedure can properly be executed by watching the ascending activation of the individual LEDs at the pressure gauge passing the point of the pressure threshold setting. For conservation of electrical energy, the LED pressure gauge can be inactivated by turning off the function key labeled "PRES" (for pressure) after the user gains adequate experience and technique in the proper compression and decompression of the compression cuff against the area of measurement. He can then feel confident by just relying on the digital readings at the proper systolic and diastolic display register. As soon as the activation of the microcomputer for the detection and enabling of the systolic and diastolic pressures including the pulse rate have been triggered after passing the level of the set pressure threshold, the acoustical transducer located in the pressure cuff means will start to detect for the first appearance of the Korotkoff sound, then amplifies the said sound as soon as it occurs, and, concurrently latches the corresponding systolic digital data at the systolic digital display register. As the Korotkoff sounds continue, the digital displays at the diastolic display register becomes enabled, proceeding in digital decrements until the diastolic level has been reached, at which instant the diastolic data gets latched at the diastolic digital display register. Both the systolic and diastolic readings are registered in one common display window as shown in 25, for example, showing a reading of 140/90. When the LED pressure gauge is activated by depressing the "PRES" function key on the "ON" position, the corresponding LED at that point or nearest that point of systolic blood pressure detection, becomes latched, and the succeeding LEDs downwards also become latched in a continuous lighted manner, describing a train of latched lighted LEDs as long as the Korotkoff sounds continue to occur until the Korotkoff sounds disappear. The latched LEDs, from the first detection of the Korotkoff sound to the disappearance of the said Korotkoff sounds provide a visual means that can be likened to a range locator, for the benefit of the user in providing him with an approximate range between the systolic and the diastolic blood pressure levels. The latched LEDs can stay in the continuously lighted manner for several seconds and will automatically fade out, or they may be cleared immediately by depressing the function key marked "C" for clear, or else they may be deactivated at the moment the user begins another pressure measuring cycle. The systolic as well as the diastolic readings including the pulse rate data are digitally displayed at 25. The other data for the "I.D. NUMBER", "DATE", "TIME", "PRESSURE THRESHOLD" and "LIMB" including the data for the main register 25 will be visibly displayed until such data is entered into the microcomputer's memory by depressing the function key labeled "E", or by depressing the function key labeled "C" in case all the displayed data is to be cancelled.

As soon as the user starts another measuring cycle for the systolic, diastolic, and pulse rate, by first reactivating the compression procedure of the pressure cuff means, the set of systolic, diastolic and pulse rate data which have just been registered will automatically be cancelled, while the other data in the independent display registers can still remain. There are three electrical sockets at the left side of the device which are shown in FIG. 1. These electrical sockets are: 3 which is for remote connection, 10 which is for connection with an external head phone when the user desires to hear the sounds more audibly without interfering with other people, or when using the device in an environment where there are undesirable noises such as in factories, or during travel, and, 9 which is for use with a battery charger that can be plugged directly to a home electrical source. While the device is connected to the battery charger which is in turn connected to the home electrical source, the system does not use the electrical power of the battery. Instead, it is being operated by the current supplied by the said home electrical source as the battery is being recharged, as long as the "PWR" function key is in the activated depressed "ON" position. Function key labeled "PTS" for the electronic pressure threshold setting, when activated in the depressed "ON" position will be ready for the electronic logging of whatever pre-selected pressure threshold setting that may be optimal for a particular subject utilizing the desired combination of the function keys from 0 to 9. Ideally, the electronic pressure threshold setting can be set therearound 30 millimeters Hg. equivalence or more, above the anticipated highest systolic blood pressure reading of the subject at his or her worst circumstantial exposure. However, in the majority of cases a pressure threshold setting of about 200 millimeters of Hg. equivalence is more than adequate a setting for most subjects, except when one is known to have a major kind of hypertension, or if one is suspected of having a quite low systolic blood pressure. The reason for the use of the distinguishing combination for right arm, left arm, right and left leg is because of the possible inherent blood pressure differences in the readings in the respective areas because of the physio-anatomic makeup of the cardiovascular system, as well as in certain pathological conditions such as in coarctation of the aorta. It is important to remember that all of the aforementioned function keys, whether in the depressed or undepressed position in cases of the two-way function keys, or in the depressed "ON" position in cases of singular function keys, can only log in the corresponding data into the microcomputer's memory by the activation of each individual function key, followed by the activation of the function key labeled "E". This can be done by pressing the "E" function key which is a momentary on/off switch. Other function keys included are the following:

(1) "TIME", which when depressed will enable the system to display the actual time at the respective digital display.

(2) "D" for date, which when depressed will activate the system to display the actual date.

(3) "CD" for clear date, when activated in the depressed "ON" position will enable the system to clear the date entered into the microcomputer in case of error in date entry during the current operation.

(4) "R", when depressed in the "ON" position will enable the system to retrieve or recall the desired I.D. code number and the particular date by the use of the appropriate combination of function keys 0 to 9, so that the blood pressure and pulse rate data, and all other associated data will automatically appear at the corresponding digital display registers.

(5) "N⟶", which when activated in the depressed "ON" position will automatically retrieve or recall the immediate next data from the date recalled according to the I.D. coding of a particular subject; said next data appearing in a sequentially forward manner as long as the said "N⟶" function key is in the "ON" position. This "N⟶" function key may remain in the depressed "ON" position until undepressed as long as the user desires, in order that all other succeeding data can automatically appear in the same sequentially forward manner as long as the said "N⟶" function key is in the "ON" position until undepressed as long as the user desires, in order that all other succeeding data can automatically appear in the same sequentially forward manner under a pre-programmed time frame (for example every 3 to 6 seconds) or whatever optimal time frame which may have been pre-programmed into the microcomputer to provide the user with an adequate time to visually assimilate the individual relevant sequence of data according to forward sequential time and date of previous measurements entered into the microcomputer's memory. This way the user will be properly informed of the data changes of the previous measurements done on a particular subject recalled within the desired time frame.

(6) "⟵N", which when depressed to attain the "ON" position will automatically retrieve or recall all relevant data at the corresponding display registers according to the date and time and I.D. code of a particular subject, in a sequentially rearward fashion for the user's comparative data reference. The appearance of the relevant data in the respective display registers with respect to time and date can also be pre-programmed at a specific time frame for the adequate utility of the user.

At 25 is a temperature display window where the temperature data is expressed in degrees of centigrade or fahrenheit, once a corresponding temperature probe has been properly attached to the temperature electrical socket 28 located at the side of the device, and also in proper placement with the right body location of the subject. Likewise, the temperature data can also be entered into the microcomputer's memory based upon the date, time, and I.D. number of the subject for future data retrieval.

A function key for temperature labeled "TEMP", and a function key for centigrade and fahrenheit, both expressed in degrees labeled "C°/F°", which is a two-way function button is provided. To operate the device in the temperature measuring mode, the function key labeled "TEMP" must be activated by depressing the said function key in the "ON" position so that the system can coordinate with the temperature probe attached to the electrical socket connector 28, as the said temperature probe is placed at certain selected parts of the subject, such as under the tongue or placed intra-rectally. When the function key "C°/F°" is in the undepressed position, the device automatically measures the subject's temperature in degrees centigrade and displays the value at the corresponding register 25. However, when the same function key is depressed, the subject's temperature is calculated and registered in degrees fahrenheit. Function key marked "I.D." when activated in the depressed "ON" position, will enable the user to enter the coded identification of the subject being tested. Another additional function key labeled "D" for date, is for the entry into the microcomputer's memory the adjusted actual date made possible by utilizing the proper combination of numbers selected from the function keys labeled 0 to 9. The real date can now proceed forward from the date of the actual setting. This works in coordination with the setting of the correct time once the function key labeled "TIME SET" has been activated in conjunction with the proper hour-minute-second setting into the microcomputer's memory with the aid of properly selected function keys ranging from 0 to 9. The function key AM/PM is a two-position function button, which when undepressed is in position to log into the memory unit the suffix AM, and when depressed, is in position to log into the memory unit the suffix PM, to correctly distinguish the AM from the PM in coordination with the proceeding hours, minutes and seconds according to the actual time set by the user in a specific geographical time zone. Function key labeled RT/LT, is also a two-way function button, which when undepressed is in position to log into the microcomputer's memory the abbreviation "RT" for right, and, which when depressed will be in position to log into the microcomputer's memory the abbreviation "LT" for left. Another two-way function button is function key A/L, which when in the undepressed state will be in position to log into the microcomputer's memory the word "ARM", and, when depressed will be in position to log into the microcomputer's memory the word "LEG". Therefore the combinations of function keys A/L and RT/LT, whether in the depressed or undepressed state, can enable the user to be able to enter into the microcomputer's memory such combinations as right arm or right leg or left arm or left leg, depending upon the limb location where the blood pressure measurement of the subject has been taken at a certain particular part of the body.

At the digital display register for "I.D. NUMBER" is a sample of a patient coded with number "008". This will distinguish this patient from any other individual for proper identification during the correct data entry and future data retrieval of the relevant data measured based on the respective date and time of measurement, including the set electronic pressure threshold of 190 mm. of Hg. equivalence used, and the limb location where the measurement was made, which in this case is shown to be at the right arm. When recalling all relevant data previously entered into the microcomputer's memory, the earliest actual time of a specific date recalled will first appear with the respective data registered at the various displays, before proceeding towards the latest actual time of that same date in cases wherein a plurality of measurements have been performed during that said date, as the function key marked "N⟶" is activated. If there was only one measurement done during that particular date recalled, the next set of data relevant to the same patient, according to the next forward sequence of time and date of measurements performed, appear at the various displays when the same function key "N⟶" continues to be activated. This sequentially forward process is achieved automatically with one set of data appearing in consecutive order within a certain pre-programmed time frame. When recalling the data of a certain patient such as the one having an I.D. number "008", based on a specific date recalled, the reverse happens when the user activates the function key marked "⟵" which means next rearwards. In this case, all relevant data displayed in the next rearward order are the ones corresponding to the latest time of the next date backwards, and then proceeding to the earliest time of that date if there were several measurements done and entered during the said next rearward date, before proceeding to the next rearward set of data of the next date going backwards. This operation will continue in a sequentially backward fashion as long as the function key "⟵N" is activated. A period of about every 3 to 6 seconds should be a sufficient time frame for displaying one set of data before proceeding to the next set of forward or backward data as the user activates the "N⟵" or "⟶N", respectively.

The memory write key labeled "MW", memory read labeled "MR" and pulse rate rhythm labeled "PRR" are additional features to those already described. The "PRR" function key, when activated will, as has already been mentioned, register the information on the regularity or irregularity of the pulse rate at the proper register within a certain pre-set time frame. The information registered includes the dynamic pulse rate value plus the computer analysis of "regular" or "irregular" for pulse rate rythm. The device can also be designed so that the "PRR" mode can work in conjunction with either or both the "PR" and the Systolic/Diastolic pressure measuring mode and then concurrently registered in the various display windows accordingly. There is also a magnetic cord slot 21 for the insertion of the magnetic card both for writing data into the card and the reading of data from the card, depending upon the I.D. number and other relevant information.

Below the function keys are found two additional slideable function keys 11 and 16, which are for logging into the device's memory the level of physical activity, and for logging into the device's memory, the level of emotional stress; both keys will have the level delineation of "LOW", "NORMAL" and "HIGH" so that the tested individuals are provided means for recording both the physical activity and the emotional stress conditions of the subject during the time of data measurement. The function keys 11 and 16 can both be slid to the proper positions indicated by the respective markings such as; 13 for "LOW", 14 for "NORMAL", 15 for "HIGH" as far as physical activity is concerned; 18 for "LOW", 19 for "NORMAL" and 20 for "HIGH" in accordance with the emotional stress of the tested individual. At 12 and 17 is shown a raised portion on the function key to aid in sliding of the indicator.

Figure 2:
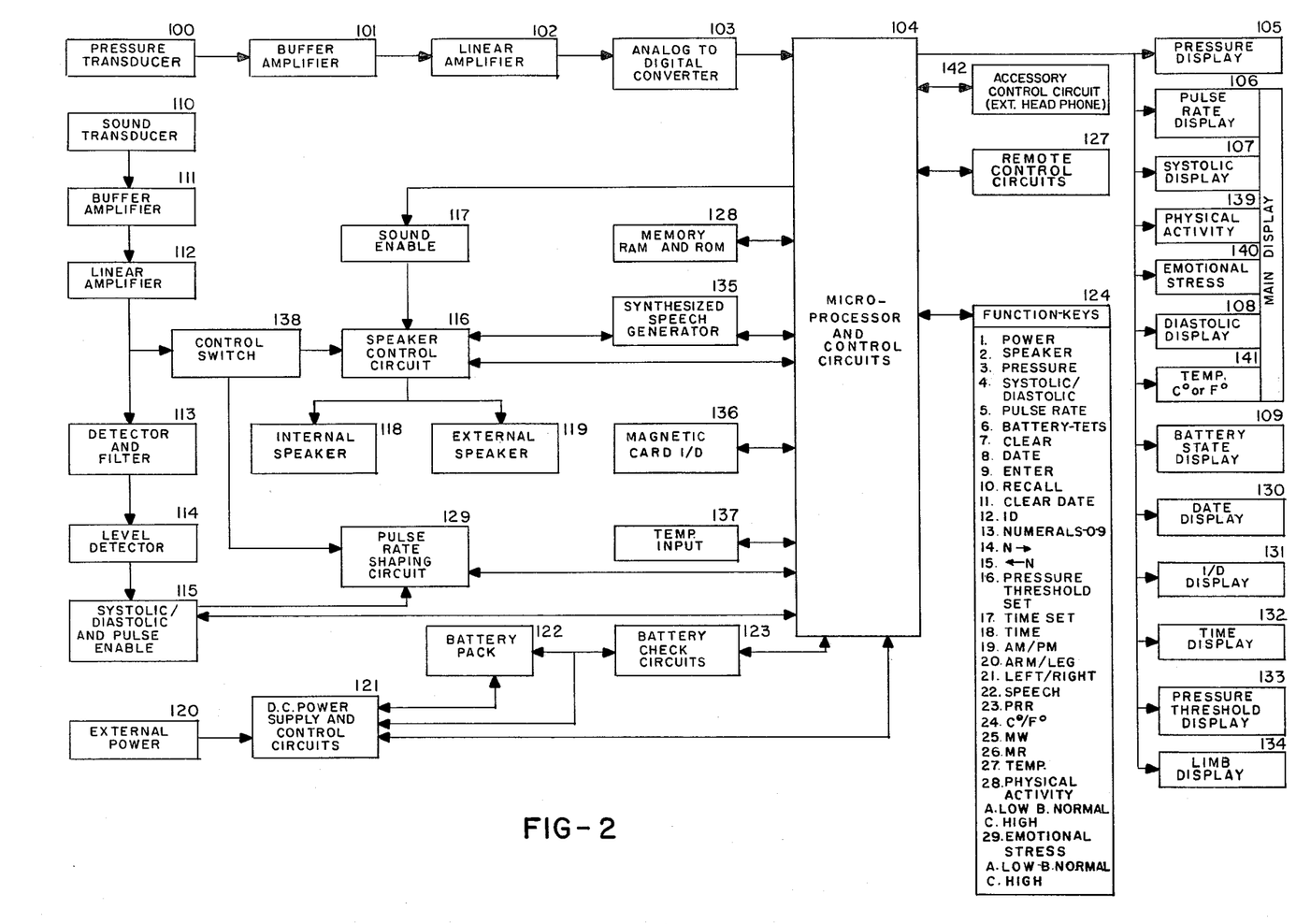
FIG. 2 is the electronic block diagram for the device in FIG. 1.

Referring now to FIG. 2 which is the electronic block diagram for the invention of FIG. 1, electrical power is supplied either by a battery pack 122 for portable operation or by an external power 120 through the appropriate regulatory electronics in 121 for operation of the device using the commercial home electrical power source as the battery pack 122 is being recharged. The activation of the whole calculator is effected by depressing the function key for "POWER" found in block 124. The pressure transducer 100 which may be a Hall-effect transducer, when activated by the displacement of the pressure cuff means against the subject's limb where the targeted artery is located produces a voltage proportional to the degree of said displacement.

The Hall-effect transducer works in conjunction with a linear spring which is factory calibrated to correspond with the appropriate pressure equivalence in millimeters of mercury compared to the commonly accepted calibration of the optimally adjusted and properly operated widely accepted mercury manometer. The voltage generated is then transmitted to the Buffer Amplifier 101 which isolates the transducer from the internal electronics as it also improves the signal condition and provides for the proper impedance matching from the said transducer to the linear amplifier 102 that provides the optimal signal gain in order to drive the analog-to-digital converter. The linear amplifier resets the linear voltage response for base preference of zero.

The voltage signal in the A/D converter becomes converted from an analog voltage signal to a binary equivalent 8-bit or 16-bit number with a range adequate enough to provide an accurate detection of the various blood pressures occurring in the human arterial system. The digital information is then transmitted to the microprocessor and control circuits in block 104 which is the heart of the calculator system of the device. The microprocessor not only receives the pressure data in digital form but also performs the proper arithmetic and logic on the data and prepares the data for distribution to the different interconnected displays. The microprocessor also anticipates the enable signals for the detection of the precise data values of both the systolic and diastolic blood pressures as well as the pulse rate.

In block 105 which is the LED pressure display, the microprocessor relays both the values of the relevant degree of compression and decompression by the pneumatic compression cuff upon the targeted vessel, as well as values of the blood pressure in dynamic form at the LED pressure display gauge. The data is continuously transmitted to the LED display activating the LEDs in succession either up or down in the calibration, one at a time until the systolic level has been reached. Once the systolic level has been detected by the acoustical transducer, the systolic enable signal latches the value of the systolic blood pressure in digital form at the systolic digital display register 107, and also latches the approximate value at the LED pressure display gauge, then the succeeding downward traveling LEDs become continuously latched in the lighted condition as the compression cuff is continuously being deflated. This light latching continues until the diastolic level has been reached, at which time the diastolic enable circuit 115 is activated to transmit the signal to the microprocessor and control circuits 104 in order that the digital readings for the diastolic blood pressure value becomes latched at the diastolic display register 108, and the LEDs below the diastolic level are not activated. The latching of the LEDs in a continuous lighted appearance from the systolic level successively downwards to the diastolic level is under the microprocessor's command. In essence, the latched lighted LEDs between the systolic and the diastolic levels acts as an approximate range locator for the convenience of the user to instantaneously show the approximate range between the systolic and the diastolic values in a visual analog manner. The latched displays, both digital and analog at the respective displays can be cleared once the function key marked "C" is activated; said LED latching continues to appear only within a certain adequate time frame, long enough for the user to be able to conveniently utilize the value of this feature.

The systolic enable circuit block 115, also activates the microprocessor to latch the digital value at block 107 which is the systolic display portion of the main display. While the systolic and the diastolic detection is being performed, the calculator also updates the dynamic digital readout at block 106, which is the main display because of the pulse enable signal coming from block 115 and going to block 129, which is the pulse rate shaping circuit that in turn transmits the signals to the microprocessor which directs the proper dynamic values of the pulse rate at the pulse rate display 106. In block 110, the sound transducer such as an acoustical transducer embedded in the compression cuff, produces a voltage proportional to the acoustical energy therearound the face of the pressure head that is in direct proximity with the targeted area. During the stethoscopic mode of the operation of the device, this transducer receives the unfiltered sounds, amplifies the signals representing the said sounds and transmits the energy to the speaker control circuit 116 to the microprocessor which activates the "SOUND ENABLE" block 117 so that the unfiltered amplified sounds of the heart beats or pulse beats as well as the respiratory rales and other respiratory sounds diagnostic of certain respiratory diseases or heart disorders can be properly transmitted to the internal speaker block 118 for audible hearing of the user. In case the user wants to use an extra headphone or earphone for better audibility and noise isolation from the external environment, the amplified sounds can be directed to the external speaker shown in block 119, once the electrical connection for the headphone or earphone has been connected to the system. The "SOUND ENABLE" block 117, the "SPEAKER CONTROL CIRCUIT" block 116, the "INTERNAL SPEAKER" block 118 and the "EXTERNAL SPEAKER" block 119 are all under the command of the microprocessor so that both input and output arrows are shown to and from the microprocessor 104 and to and from the speaker control circuits 116. The unfiltered amplified sounds emanating from both the targeted artery such as the radial artery or the heart sounds emanating or being detected from the chest, as well as the respiratory sounds also detected at the chest area can be audibly heard even without activation of the compression cuff means 2 during both the stethoscopic mode and the pulse rate mode of operation of the device because the control switch block 138 closes the electrical circuit going to the pulse rate shaping circuit 129 and the speaker control circuit 116, thus allowing the transmission of sounds and the counting of the pulses without passing through block 113. However, in the pressure measuring mode in coordination with the pulse rate measuring mode, the activation of the systolic/diastolic function key represented by number 4 of block 124, automatically commands the microprocessor 104 to open the control switch 138 so that no signal goes to block 129 and block 116.

It is important to note that no sounds will be heard through the external speaker nor the internal speaker, unless the function key numbered 2 for "SPEAKER" in block 124 has been depressed in the "ON" position no matter what mode of operation the device may be in. When the device is only in the pulse rate mode, achieved by activating the pulse rate function key numbered 5 of block 124 and the "SPEAKER" function key numbered 2 of block 124 is in the depressed "ON" position; the device can function like an electronic stethoscope and the sounds are enabled through either of the speakers, plus the capability of having a dynamic readout of the pulse rate or heart rate per minute. The sounds of the pulse beats and the heart beats including the respiratory sounds are picked up by the sound transducer 110 and the signals are directed through buffer amplifier 111 and linear amplifier 112 through the closed circuit of block 138 to the speaker control circuit 116 to the microprocessor 104 through the sound enable 117 to 116 and then to either 118 or 119.

When the calculator has been activated to function in the pressure measuring mode as well as the pulse rate measuring mode, both function keys marked Systolic/Diastolic and the pulse rate function key of block 124 are depressed in the "ON" position so that the systolic and the diastolic blood pressures can be determined concurrently with the pulse rate through the detection of the Korotkoff sounds while the subjected artery such as the brachial artery is being gradually deoccluded from the state of total non-invasive occlusion secondary to the degree of compression exerted by the compression cuff against the aforesaid targeted vessel. The sound transducer 110 permits the detection of the associated Korotkoff sounds emitted because of the closing and gradual opening of the pressurized arterial vessel causing intra-arterial turbulent blood flow across the semi-open lumen of the vessel. The Korotkoff sounds are channeled to the buffer amplifier 111 which isolates the transducer from the internal electronics as it improves the signal condition and provides for the proper impedance matching from the transducer to the linear amplifier 112 which offers the adequate signal gain in order to drive the detector and the control circuits to achieve sufficient distinguishable rise and fall time of the audio for the proper detection of both the systolic and the diastolic levels.

The signals are then channeled to the detector and filter 113, wherein the audio is detected and then filtered in a normal method leaving a distinguishable envelope with the significant rise and decay. The signal is then transmitted to the level detector 114, wherein the detected signal becomes monitored for the distinguishable rate of increase in signal so that within milliseconds of detection the systolic enable 115 becomes activated, and then, as the signal proceeds through its decay period, the level detector evaluates each succeeding sample signal until the time that there is no change in samples determined which implies that the disappearance of the Korotkoff sounds has already been reached, activating the diastolic enable circuit 115 within milliseconds, so that the diastolic data can be latched into the proper display. The signals from the level detector 114 is sent to the systolic/diastolic and pulse enable 115 directly to the microprocessor and control circuit 104 as well as to the pulse rate shaping circuit 129. Both the systolic and the diastolic digital values are displayed in the systolic display 107 and the diastolic display 108 as enabled by 115 through the microprocessor 104. The pulse rate digital readout which is an updated dynamic value is displayed at 106 after passing through the pulse rate shaping circuit 129 through the microprocessor and control circuits 104. The systolic/diastolic and pulse enable 115 sends the pulse signals to 129 during the same time frame of systolic and diastolic blood pressures measurement, and after directing the signals to 104, the approximate LEDs at the LED pressure gauge are latched successively from the systolic to the diastolic levels giving an appearance of a train of lighted LEDs from the systolic level to the diastolic level located at the LED pressure display gauge. The digital values for the displays 106, 107, and 108 also becomes latched until a new measurement cycle is made or until the system is cleared.

When the device is in the pulse rate measuring mode, the detected audio is converted to a distinguishable square-wave pulse form which in turn becomes detected by the microprocessor as a distinguishable pulse; the succeeding pulses are measured for their pulse period thus enabling the calculator to arrive at a dynamic pulse rate measurement.

The threshold setter in this case is electronically set to a certain pressure level approximately thirty or more millimeters Hg. of pressure equivalence above the subject's anticipated highest systolic blood pressure. The pressure threshold set is detected by the microprocessor so that the required threshold voltage that is critical to the pressure measurement becomes set into the microcomputer's memory enabling the system to be fully activated for the proper systolic, diastolic and pulse rate measurements only after the set pressure threshold has been exceeded by the values of the pressure exerted by the pressure head applying means. This is a means of conserving electrical energy when the system is operating in the coordinated systolic, diastolic and pulse rate measuring mode.

The device can also operate by connecting it to a regular commercial power designated by block 120 which supplies the electricity to the system, passing through D.C. power supply and control circuits represented by block 121. Standard D.C. power supply electronics and voltage regulation are provided for the distribution of the appropriate voltages for the microprocessor, electronic circuits, transducers, and displays. The battery pack 122 supplies the electrical power for the appropriate portable operation of the device. When external power is connected to the system, the battery pack gets recharged, as the device runs on commercial power. The battery check circuit 123 is electrically connected to the battery pack and the microprocessor hence when the function key marked "Bat Test" for battery test shown in 124 is activated, an appropriate load of electrical current and voltage is applied on the battery pack, evaluating the rate of change of both voltage and current of the said battery pack. When the battery pack has sufficient electrical energy to run the device in an optimal manner, the microprocessor enables the transmission of a continuous sound through the internal speaker or external speaker, after passing through the "Speaker Control Circuit" 116; and "sound enable" block 117 to the microprocessor which also activates the appearance of a continuous light display concurrently at the "battery state display" 109. If the battery pack's electrical energy is running low and the batter test function key numbered 6 in block 124 is activated, the battery check circuit 123 sends signals to the microprocessor to automatically trigger the emission of intermittent beeping sounds through the speaker control circuit to either the internal speaker or the external speaker, and at the same time an intermittent or blinking light is initiated by the microprocessor at 29. This constitutes a warning system for the user in determining the electrical capabilities or potentials of the battery pack for adequate portable use, so that the necessary replacement of the battery pack or the recharging of the same by means of connecting the device to an external power source can be properly done.

Block 128 represents the calculator's RAM and ROM memory which is electrically interlinked in a two-way direction with the microprocessor and control circuits 104.

Block 127 is for remote control circuit which is electrically connected in a two-way electrical direction with the microprocessor and control circuits for adaptation to external display input-output system including such devices as tape recorder, video monitors, etc.

The function keys are interconnected in a two-way direction with the microprocessor and control circuits in order that the microprocessor can continuously interrogate the various function keys and their current status of activation while certain activated function keys relay the command to the said microprocessor and control circuits for the achievement of greater speed and better control.

The electronic pressure threshold setter function key in block 124 and numbered 16, when activated, enables the system to use function keys having numerals 0 to 9 and log into the microcomputer's memory (RAM) the desired electronic pressure threshold digital setting.

There are additional function keys in block 124 enumerated from numbers 22 to 29 as well as additional detection capability for the temperature of the subject registerable at 25 expressed selectively either in centigrade or fahrenheit degrees when the device is in the temperature measuring mode, which is achieved when the function key marked "TEMP" is activated together with the function key marked "C°/F°" while the appropriate temperature probe has been properly placed upon the desired spot of the subject's body and the electrical connector of the said probe has been properly linked into the electrical socket of the system.

The magnetic card input/output 136 communicates with the microprocessor and control circuits for proper magnetic card data entry when the function key "MW" numbered 25 of block 124 is activated, and the retrieval of same data when the "MR" function key numbered 26 of block 124 is activated. Temperature input 137 also communicates with the microprocessor and control circuits for the temperature input data, either in degrees centigrade or fahrenheit, to be registered at 25. Other function keys are as follows: Function key for speech numbered 22 of block 124 shown as "SPCH" in FIG. 1, which when depressed will enable the system to activate the synthesized speech generator 135 through the microprocessor and control circuits to the speaker controls in order that the data retrieved can be heard through either the internal or external speakers; function key numbered 23 for pulse rate and rhythm of block 124 which when activated in the "ON" position will command the microprocessor to display the regularity or irregularity of the pulse rate at the main display at the same time, will give the numerical calculations of the pulse rate per minute reading at the pulse rate display; physical activity function key numbered 28 of block 124 which when activated will be able to delineate three levels of physical activity such as low, normal, and high depending upon the physical condition of the subject during the time of blood pressure and pulse rate measurement, said data capable of being entered into the microcomputer's memory for future data retrieval, said physical activity delineation capable of being displayed at the main register; emotional stress function key numbered 29 which when activated in the "ON" position will be able to delineate in various switch positions as to the emotional level of the tested individual as far as either being at the low, normal, or high stress during the measuring cycle of the operation, said data can be properly displayed into the main display of the device and also capable of being entered into the microcomputer's memory through the microcomputer for future data retrieval.

The accessory control circuit 142 is for adaptation with the output to the external headphone or earphone.

It is important to note that although the instant invention has been described, modification and other applications of the invention will be obvious to those skilled in the art and are herewith included within the spirit and the scope of the invention whether it may be for current use or for future use as long as the said embodiments, modifications, and applications are within the perimeters of the present invention as defined by the appended claims.

What is claimed is:

1. An electronic blood pressure and pulse rate measuring device for use on a subject by a user who can be said subject or another person and that can be used with battery power or ordinary available home and office current which comprises, in combination; an inflatable-deflatable circumferentially adaptable arm-cuff with detachable acoustical transducer means to detect the first appearance of the Korotkoff sounds and the disappearance of the Korotkoff sounds including the series of Korotkoff sounds occuring therebetween for measuring the systolic and diastolic blood pressure and pulse rate of the subject, a pressure sensing means for transforming the degree expressed in millimeters of mercury of the pressure of the cuff upon the subjected arm to correlate with both analog and digital readings indicative of the first appearance and the disappearance of the Korotkoff sounds produced by the semioccluded artery and its gradual deocclusion process, a pressure threshold setting means which can electronically be programmed or set by the user at about the equivalence of 20 millimeters of mercury reading or higher above the anticipated highest systolic blood pressure reading of the subject, whereupon said programmed threshold reading upon having been exceeded by the arm cuff's compression pressure exerted therearound the arm or limb of the subject, said pressure threshold setting means will automatically trigger or activate the electronic circuitry of the system to sense for and latch the systolic and the diastolic readings by a systolic enabling circuit and a diastolic enabling circuit, respectively and, within the time frame of the systolic and diastolic measurement, means for calculating arithmetically the pulse rate per minute of the subject based on the pulses and rate of the appearance of the Korotkoff sounds as picked up by the acoustical transducer means, a physical activity degree delineation means that enables the user to program the degree of physical activity of the subject during the time and data of the blood pressure and pulse rate measurement, so that upon entry and storage of this valuable data in correlation with the subject's ID number and the date and time of blood pressure and pulse rate measurement, it is possible to retrieve or recall the the combinations of those data at a later date for comparative purposes, an emotional stress degree delineating means that enables the user to program the degree of emotional stress of the subject during the time and date of the blood pressure and pulse rate measurement, so that upon entry and storage of this valuable data in correlation with the subject's ID number and the data and time of blood pressure and pulse rate measurements, it is possible to retrieve or recall the combinations of these data at a later date for comparative purposes, means of recalling the desired combination data either singly or in multiples in forward sequential or rearward sequential order relevant to a pre-programmed rate of consecutive appearances of data display, important for use by user for comparative purposes, a means for calculating the regularity or irregularity of the pulse rate including means for entering and storing pulse rate regularity and irregularity data and retrieving of the same at a later date, light emitting means for visually establishing the range between the systolic blood pressure reading and the diastolic blood pressure reading by the appearance of a plurality of continuously latched light signals starting from the systolic blood pressure reading to the diastolic blood pressure reading as correlated to a linear gauge enabling the user the capability of a visual representation of the approximate range and disparity between the subject's systolic and diastolic readings, a means of programming the correct right or left arm location where the blood pressure is being taken, respectively during the blood pressure measurement, before and during entry of this data into memory together with the other data relevant to a particular subject so that upon future retrieval of the combination of this data, the user can be reminded from which arm the particular blood pressure was taken according to the particular time and date of measurement.

2. A non-invasive electronic blood pressure and pulse rate calculator utilizing a combination of a circumferentially adaptable inflatable-deflatable arm-cuff to detect the systolic and diastolic blood pressure and pulse rate readings by the Korotkoff method through a combination of pressure and acoustical transducers correlated with calibration means in equivalence of millimeters of mercury, wherein the readings can be programmed to coordinate with an electronic means of grading the degree of physical activity and (or) the degree of emotional stress of the subject before each measurement is taken so as to coordinate this data with the patient identification at certain times and dates for entry and storage into the calculator's memory for future coordinated retrieval either for singular data display or multiple data display retrievable in either forward or backward order in time according to the programmed time frame of interval between each group of correlated data.

3. An electronic blood pressure and pulse rate measuring device for use on a subject by a user who can be said subject or another person and that can be used with battery power or ordinary available home and office current which comprises, in combination; an inflatable-deflatable circumferentially adaptable arm-cuff with detachable acoustical transducer means to detect the first appearance of the Korotkoff sounds and the disappearance of the Korotkoff sounds including in series of Korotkoff sounds occuring therebetween for measuring the systolic and diastolic blood pressure and pulse rate of the subject, a pressure sensing means for transforming the degree expressed in millimeters of mercury of the pressure of the cuff upon the subjected arm to correlate with both analog and digital readings indicative of the first appearance and the disappearance of the Korotkoff sounds produced by the semi-occluded artery and its gradual deocclusion process, a pressure threshold setting means which can electronically be programmed or set by the user at about the equivalence of 20 millimeters of mercury reading or higher above the anticipated highest systolic blood pressure reading of the subject, whereupon said programmed threshold reading upon having been exceeded by the arm cuff's compression pressure exerted therearound the arm or limb of the subject, said pressure threshold setting means will automatically trigger or activate the electronic circuitry of the system to sense for and latch the systolic and the diastolic readings by a systolic enabling circuit and a diastolic enabling circuit, respectively and, within the time frame of the systolic and diastolic measurement, means for calculating arithmetically the pulse rate per minute of the subject based on the pulses and rate of the appearance of the Korotkoff sounds as picked up by the acoustical transducer means, a physical activity degree delineation means that enables the user to program the degree of physical activity of the subject during the time and date of the blood pressure and pulse rate measurement, so that upon entry and storage of this valuable data in correlation with the subject's ID number and the date and time of blood pressure and pulse rate measurement, it is possible to retrieve or recall the combinations of these data at a later date for comparative purposes, an emotional stress degree delineating means that enables the user to program the degree of emotional stress of the subject during the time and date of the blood pressure and pulse rate measurement, so that upon entry and storage of this valuable data in correlation with the subject's ID number and the date and time of blood pressure and pulse rate measurements, it is possible to retrieve or recall the combinations of these data at a later date for comparative purposes, a means of recalling the desired combination data either singly or in multiples in forward sequential or rearward sequential order relevant to a pre-programmed rate of consecutive appearances of data display, important for use by the user for comparative purposes, a means for calculating the regularity or irregularity of the pulse rate including means for entering and storing pulse rate regularity and irregularity data and retrieving of the same at a later date, a means of programming the correct right or left arm location where the blood pressure is being taken, respectively during the blood pressure measurement, before and during entry of this data into the memory together with the other data relevant to a particular subject so that upon future retrieval of the combination of this data, the user can be reminded from which arm the particular blood pressure was taken according to the particular time and date of measurement.

* * * * *